(12) United States Patent
Arcaro et al.

(10) Patent No.: US 11,104,104 B2
(45) Date of Patent: Aug. 31, 2021

(54) CONTAINER FOR EMANATING VOLATILE SUBSTANCES

(71) Applicant: AMCOR FLEXIBLES ITALIA S.R.L., Lugo di Vicenza (IT)

(72) Inventors: Alberto Arcaro, Padua (IT); Galina Ourieva, Amougies (BE); Thomas Fessler, Constance (DE)

(73) Assignee: Amcor Flexibles Italia S.R.L., Lugo di Vicenza (IT)

( * ) Notice: Subject to any disclaimer, the term of this patent is extended or adjusted under 35 U.S.C. 154(b) by 178 days.

(21) Appl. No.: 16/348,722

(22) PCT Filed: Nov. 24, 2017

(86) PCT No.: PCT/EP2017/080432
§ 371 (c)(1),
(2) Date: May 9, 2019

(87) PCT Pub. No.: WO2018/096128
PCT Pub. Date: May 31, 2018

(65) Prior Publication Data
US 2019/0366689 A1    Dec. 5, 2019

(30) Foreign Application Priority Data
Nov. 25, 2016 (EP) .................................. 16020466

(51) Int. Cl.
*B32B 15/09* (2006.01)
*A61L 9/12* (2006.01)
(Continued)

(52) U.S. Cl.
CPC .............. *B32B 15/09* (2013.01); *A61L 9/12* (2013.01); *B32B 7/06* (2013.01); *B32B 7/12* (2013.01);
(Continued)

(58) Field of Classification Search
CPC ..... A61L 9/04; A61L 9/12; B32B 7/06; B32B 7/12; B32B 15/09; B32B 15/20;
(Continued)

(56) References Cited

U.S. PATENT DOCUMENTS 5,395,047 A * 3/1995 Pendergrass, Jr. ........ A61L 9/12
239/34
5,518,790 A * 5/1996 Huber ....................... A61L 9/12
239/55
(Continued)

FOREIGN PATENT DOCUMENTS

| CN | 1246091 A | 3/2000 |
|----|-----------|--------|
| WO | WO199823304 A1 | 6/1998 |
| WO | WO200009174 A1 | 2/2000 |

*Primary Examiner* — Steven J Ganey

(57) ABSTRACT

The invention relates to a container for emanating volatile substances, The container comprises a container body which has at least one opening and is closed by a lid film. The lid film comprises an outer multi-layer film having at least one barrier layer impermeable to the volatile substances, a coextruded inner multi-layer film having at least one layer permeable to the volatile substances. The coextruded inner multi-layer film is bonded on one side to the outer multi-layer film and on another side to the container. The coextruded inner multi-layer film consists of at least a polyethylene layer, a release layer comprising a polymer selected from the group consisting of EVOH and PETg, a peelable interface interposed between the release layer and a layer permeable to the volatile substances, whereby said permeable layer comprises a polymer selected from the group consisting of mVLDLLDPE, ethylene vinyl acetate copolymer, and ethylene n-butyl acrylate copolymer.

14 Claims, 4 Drawing Sheets

(51) Int. Cl.
*B32B 7/06* (2019.01)
*B32B 7/12* (2006.01)
*B32B 15/20* (2006.01)
*B32B 27/30* (2006.01)
*B32B 27/32* (2006.01)
*B32B 27/36* (2006.01)
*B65D 65/40* (2006.01)

(52) U.S. Cl.
CPC ............ *B32B 15/20* (2013.01); *B32B 27/306* (2013.01); *B32B 27/32* (2013.01); *B32B 27/327* (2013.01); *B32B 27/36* (2013.01); *B65D 65/40* (2013.01); *B32B 2255/10* (2013.01); *B32B 2255/20* (2013.01); *B32B 2307/412* (2013.01); *B32B 2307/724* (2013.01); *B32B 2307/7265* (2013.01); *B32B 2307/748* (2013.01); *B32B 2435/02* (2013.01)

(58) Field of Classification Search
CPC ..... B32B 27/306; B32B 27/32; B32B 27/327; B32B 27/36; B65D 65/40
USPC ..... 239/34, 53, 55; 422/123; 428/41.8, 41.7, 428/905
See application file for complete search history.

(56) References Cited

U.S. PATENT DOCUMENTS

| | | | | |
|---|---|---|---|---|
| 5,782,409 | A * | 7/1998 | Paul | A61L 9/12 |
| | | | | 428/905 |
| 5,804,262 | A | 9/1998 | Stevens | |
| 6,638,591 | B2 * | 10/2003 | Bowen | A61L 9/12 |
| | | | | 239/34 |
| 6,722,578 | B2 * | 4/2004 | Skalitzky | A61L 9/03 |
| | | | | 239/53 |
| 7,980,486 | B2 * | 7/2011 | Trent | A61L 9/03 |
| | | | | 239/55 |

* cited by examiner

CONTAINER FOR EMANATING VOLATILE SUBSTANCES

The present invention relates to a container for emanating volatile substances.

Containers for emanating volatile substances are known in the art. Usually, such containers comprise a lid film which closes the opening and prevents emanation of the volatile substance housed in the container until the container is activated to release the volatile substances. To activate the container, the lid film is removed either as a whole or at least in part. Of course, it is desirable that not the whole lid film is removed as the total removal of the lid film creates an unprotected opening which may lead to unwanted spillage of the stored volatile substances. Therefore, usually a part of the lid film remains on the opening protecting the user from unwanted spillage and contact with the volatile substances. The remaining part, however, reduces the evaporation rate of the volatile substances thereby limiting a fast distribution of the volatile substances and thus limiting the consumer perception. There is a need for lid films protecting the opening of the container thus avoiding spillage of or direct contact with the volatile substances by the consumer without limiting the evaporation rate of the volatile substances once the container is activated and the barrier part of the lid film is removed.

The aim of the present invention is to overcome the problems found in the prior art. An important object of the present invention is to provide a container with a lid film which easily and consistently separates between the barrier part and the permeable part of the lid film. A further object is to provide a lid film where the remaining permeable part allows a maximal evaporation of the stored volatile substances.

The objects are achieved by a container as defined in claim 1. Further embodiments are subject of the dependent claims.

A container for emanating volatile substances comprises a container body which has at least one opening. The opening is closed by a lid film. Said lid film comprises an outer multi-layer film that includes at least one barrier layer which is impermeable to the volatile substances. The lid film further comprises a coextruded inner multi-layer film with at least one layer that is permeable to the volatile substances. The coextruded inner multi-layer film is bonded on one side to the outer multi-layer film. On the other side the coextruded inner multi-layer film is bonded to the container. The coextruded inner multi-layer film consists of at least polyethylene layer, a release layer which comprises a polymer that is selected of the group consisting of polyethylene vinyl alcohol (EVOH) and polyethylene terephthalate glycol modified (PETg), a peelable interface which is interposed between the release layer and a layer that is permeable to the volatile substances. Said permeable layer comprises a polymer selected from the group consisting of metallocene very low density linear low-density polyethylene (mVLDLLDPE), ethylene vinyl acetate copolymer (EVA), and n-butyl acrylate copolymer (EBA). The permeable layer is sealed on one side to the container and provides an evaporation rate of the volatile substances of at least 30% of a maximal evaporation rate of an opening not covered by said permeable layer.

The acronyms used herein refer to and are understood as follows, EVOH refers to polyethylene vinyl alcohol, PETg to polyethylene terephtalate glycol modified, EVA to ethylene vinyl acetate copolymer, and EBA to n-butyl acrylate copolymer. LDPE refers to low-density polyethylene, LLDP to linear low-density polyethylene, and mVLDLLDPE to metallocene very low-density linear low-density polyethylene. The latter is understood as a polyethylene polymer which is substantially linear and has a very low density and which has been synthesized using a metallocene catalyst. The metallocene very low-density linear low-density polyethylene (mVLDLLDPE) may also designated as metallocene very low-density polyethylene (mVLDPE). Polyethylene is also classified according to its density, very low-density polyethylene has a density below 0.91 g/cm$^3$, low-density polyethylene has a density in the range of 0.91 g/cm$^3$ and 0.94 g/cm$^3$, whereas polyethylene with a density higher than 0.94 g/cm$^3$ is termed high-density polyethylene.

The peelable interface may be achieved by a peelable resin layer. But it may also be achieved by direct bonding between the release layer and the permeable layer.

The maximal evaporation rate is defined as the evaporation rate achieved if the opening through which the volatile substances evaporate is not covered, i.e. there is no membrane present at all which covers the opening. This is the maximum evaporation rate that may be achieved at a given set of ambient conditions such as temperature and relative humidity.

Usually, the evaporation rate is measured at ambient temperature. The temperature may also be held constant at 25° C. In addition, the relative humidity may also be held constant at 50%. The measurement is then performed by filling a defined amount of a volatile substance or composition in an appropriate container, whereby the opening is subsequently firmly covered with the membrane which is to be tested. The weight of the container filled with the volatile composition and its opening firmly covered with the membrane to be tested is measured at the beginning and subsequently at defined time intervals until either all the volatile composition is evaporated or until the end of a defined time period. The weight loss over time indicates the evaporation rate.

Preferably, the evaporation rate of the volatile substances is at least 40%, preferably 50%, more preferably 60% and most preferably 70% of a maximal evaporation rate of an opening not covered by a permeable layer.

In a further embodiment, the permeable layer comprises an outer layer, a core layer and a sealing layer. The outer layer is made of polymer blend of mVLDLLDPE, LDPE, and LLDPE. The core layer of the permeable layer is made of a polymer blend of mVLDLLDPE, and LLDPE. The core layer may also be made of a polymer blend of mVLDLLDPE and LDPE. Polymer blends for the core layer made of mVLDLLDPE and LLDPE are preferred. And the sealing layer of the permeable layer is made of a polymer blend of mVLDLLDPE, LDPE, and LLDPE. The sealing layer of the permeable layer is sealed to the container.

In another embodiment, the polymer blend of the outer layer comprises 10-30 weight-% mVLDLLDPE, 60-80 weight-% LLDPE, and 10 weight-% LDPE. The polymer blend of the core layer comprises 30-65 weight-% mVLDLLDPE, and 35-70 weight-% LLDPE, and the polymer blend of the sealing layer comprises 10-30 weight-% mVLDLLDPE, 60-80 weight-% LLDPE, and 10 weight-% LDPE. The total content of mVLDLLDPE in the permeable layer is in the range of 10-90 weight percent, preferably in the range of 30-60 weight-%.

In yet a further embodiment, the permeable layer comprises an optional outer layer made of LDPE or LLDPE, a core layer made of a polymer blend of EVA and PE, and an optional sealing layer made of LDPE or LLDPE.

In another embodiment, the permeable layer comprises an optional outer layer comprising LDPE or LLDPE and optionally up to 30 weight-% EVA, a core layer made of a polymer blend of EVA and PE, and an optional sealing layer comprising LDPE or LLDPE and optionally up to 30 weight-% EVA.

In another embodiment, that the core layer consists of a blend of EVA in range of 10-90 weight-%, preferably in the range of 30-70 weight-%, and the remainder PE. The vinyl acetate content in the EVA copolymer is preferably 18% vinyl acetate of the total monomers.

In a further embodiment, the permeable layer comprises an optional outer layer made of LDPE or LLDPE, a core layer made of a polymer blend of EBA, PE, and an optional sealing layer made of LDPE or LLDPE.

In another embodiment, the permeable layer comprises an optional outer layer comprising LDPE or LLDPE and optionally up to 30 weight-% EBA, a core layer made of a polymer blend of EBA and PE, and an optional sealing layer comprising LDPE or LLDPE and optionally up to 30 weight-% EBA.

Advantageously, the core layer consists of a blend of EBA in the range of 10-90 weight-%, preferably in the range of 30-70 weight-%, and the remaining part of the polymer blend comprises PE.

In another embodiment, the outer multi-layer film comprises a first PET layer, an aluminum layer as barrier layer to the volatile substances, and a second PET layer.

In yet a further embodiment, the outer multi-layer film comprises a PET layer and a transparent barrier layer. Such a transparent barrier layer may consist of a $SiO_x$ coated second PET layer which is bonded to the first PET layer such that the $SiO_x$ coating, constituting the barrier, is interposed between the two PET layers.

In another embodiment, the outer multi-layer comprises a PET layer and a second $AlO_x$ coated PET layer. The $AlO_x$ coating which provides the barrier function to the volatile substances is interposed between the two PET layers.

Further suitable barrier layers may be obtained with metalized plastic layers, preferably metalized PET layers or metalized polypropylene layers.

In another embodiment, there is a small non-bonded region between the release layer and the permeable layer. This small non-bonded region provides a grip tab for the separation of the lid film between the release layer and the permeable layer.

The container according to the invention will be explained in more detail in the following text with reference to exemplary embodiments which are illustrated in the drawings and in which, purely schematically:

Figure 1:
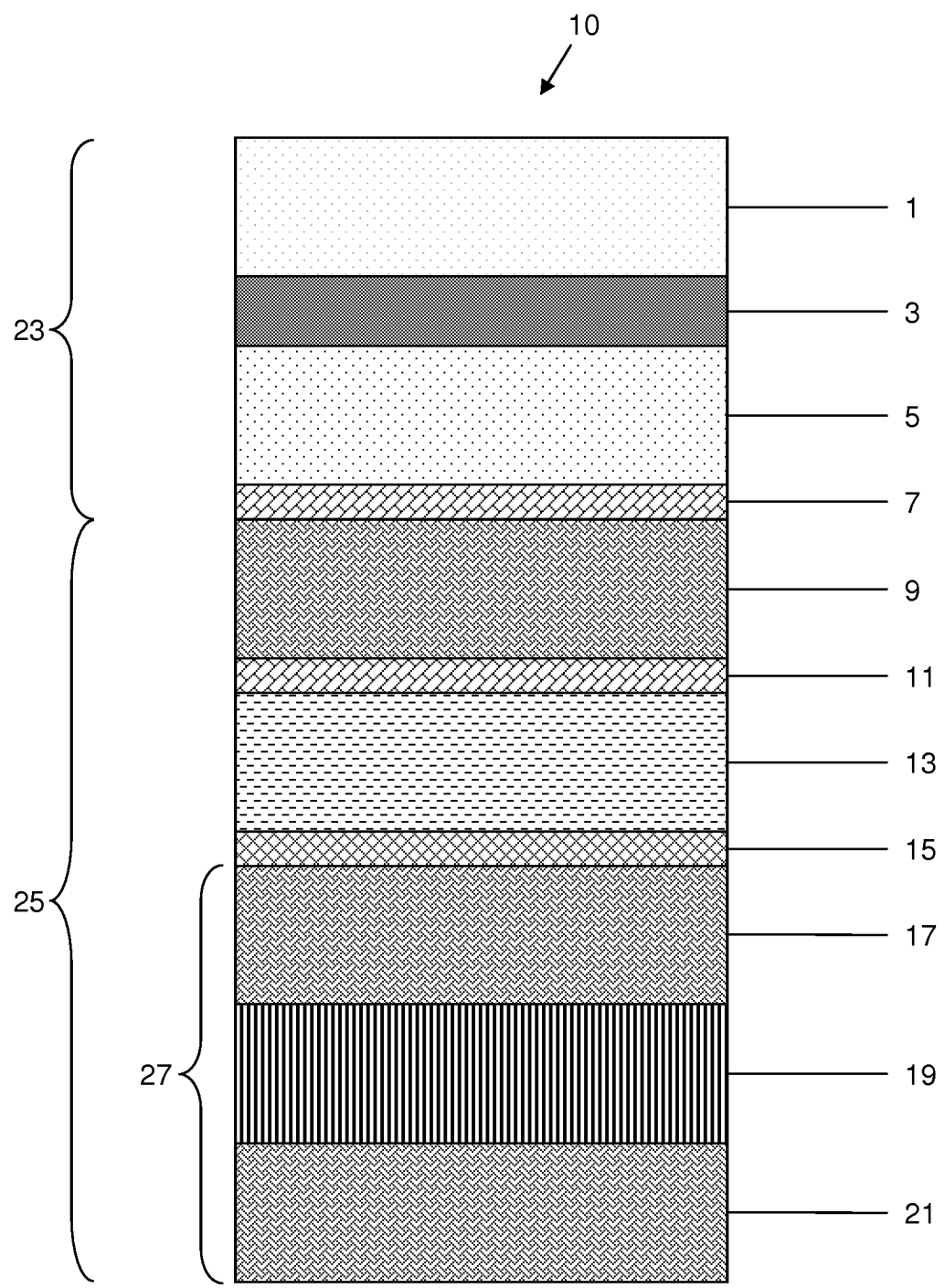
FIG. 1 shows a cross-sectional view of a first embodiment of the lid film.

FIG. 1 shows a cross-sectional view of a first embodiment of the lid film 10 according to the present invention. The lid film 10 comprises an outer multi-layer film 23 bonded to a coextruded inner multi-layer film 25. A permeable layer 27 which itself comprises in the embodiment shown three layers is a part of the coextruded inner multi-layer film 25. The layers of the lid film 10 comprise from the outside to the inside the following layers, a PET layer 1, a barrier layer 3 which consists of an aluminum foil, a second PET layer 5. These layers constitute the outer multi-layer film 23 of the lid film 10. The outer multi-layer film 23 is bonded by means of an adhesive layer 7 to the coextruded inner multi-layer film 25 which comprises in sequential order from outside to inside a polyethylene layer 9, an adhesive layer 11, a release layer 13, a peelable interface 15 and a permeable layer 27, whereby the peelable interface is interposed between the release layer 13 and the permeable layer 27. Said permeable layer 27 comprises itself three layers, an outer layer 17, bonded by the peelable interface 15 to the release layer 13, a core layer 19 and a sealing layer 21. The sealing layer 21 is sealed to a container (not shown) housing the volatile substances.

Figure 2:
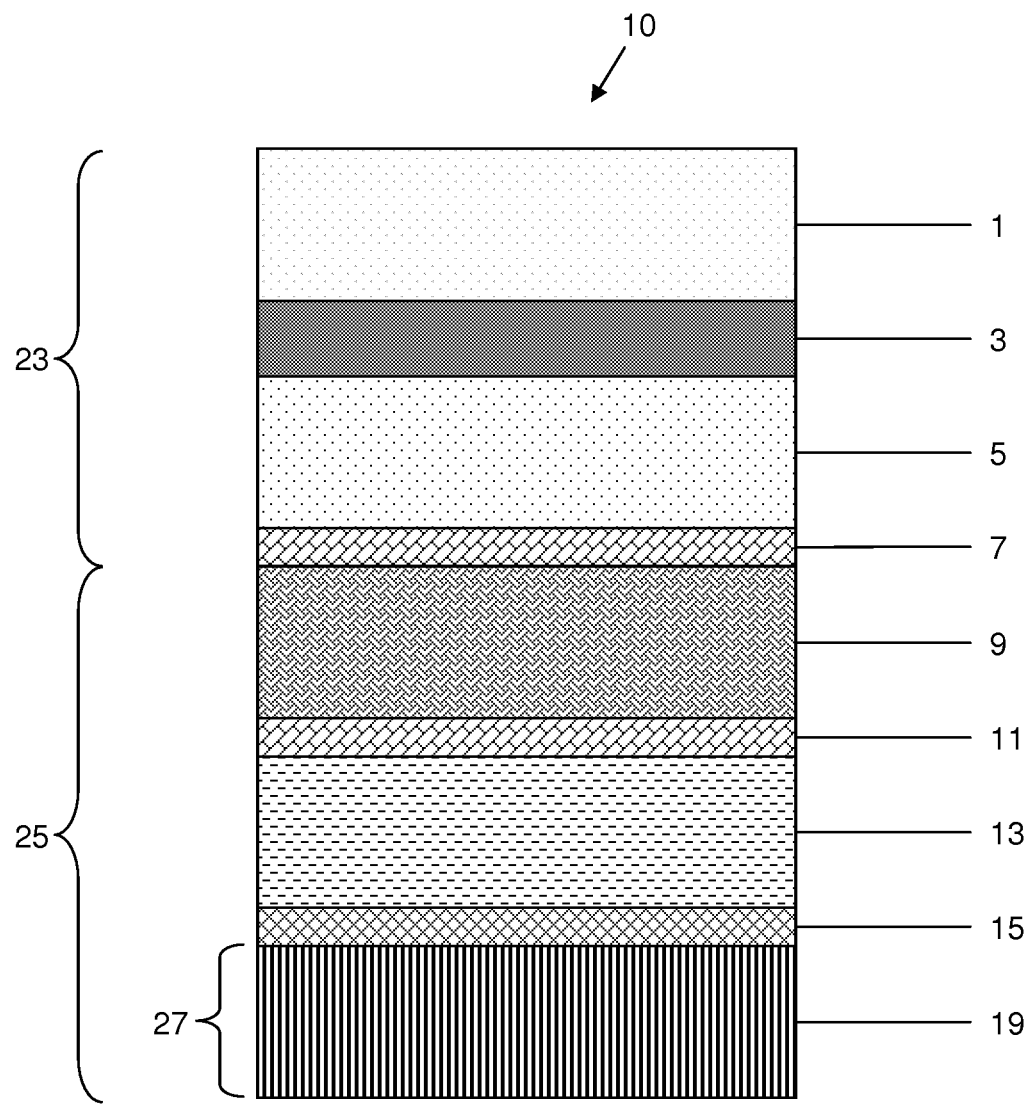
FIG. 2 shows a cross-sectional view of a second embodiment of the lid film.

FIG. 2 shows a cross-sectional view of a second embodiment of the lid film 10. The outer multi-layer film 23 is the same as shown in FIG. 1. In contrast to the embodiment shown in FIG. 1 the coextruded inner multi-layer film comprises a permeable layer 27 consisting of a single core layer 19 which is directly bonded via the peelable interface 15 to the release layer 13. The permeable layer 27 consisting of the single core layer 19 is sealed to the container (not shown) and thus faces a product space (not shown).

Figure 3:
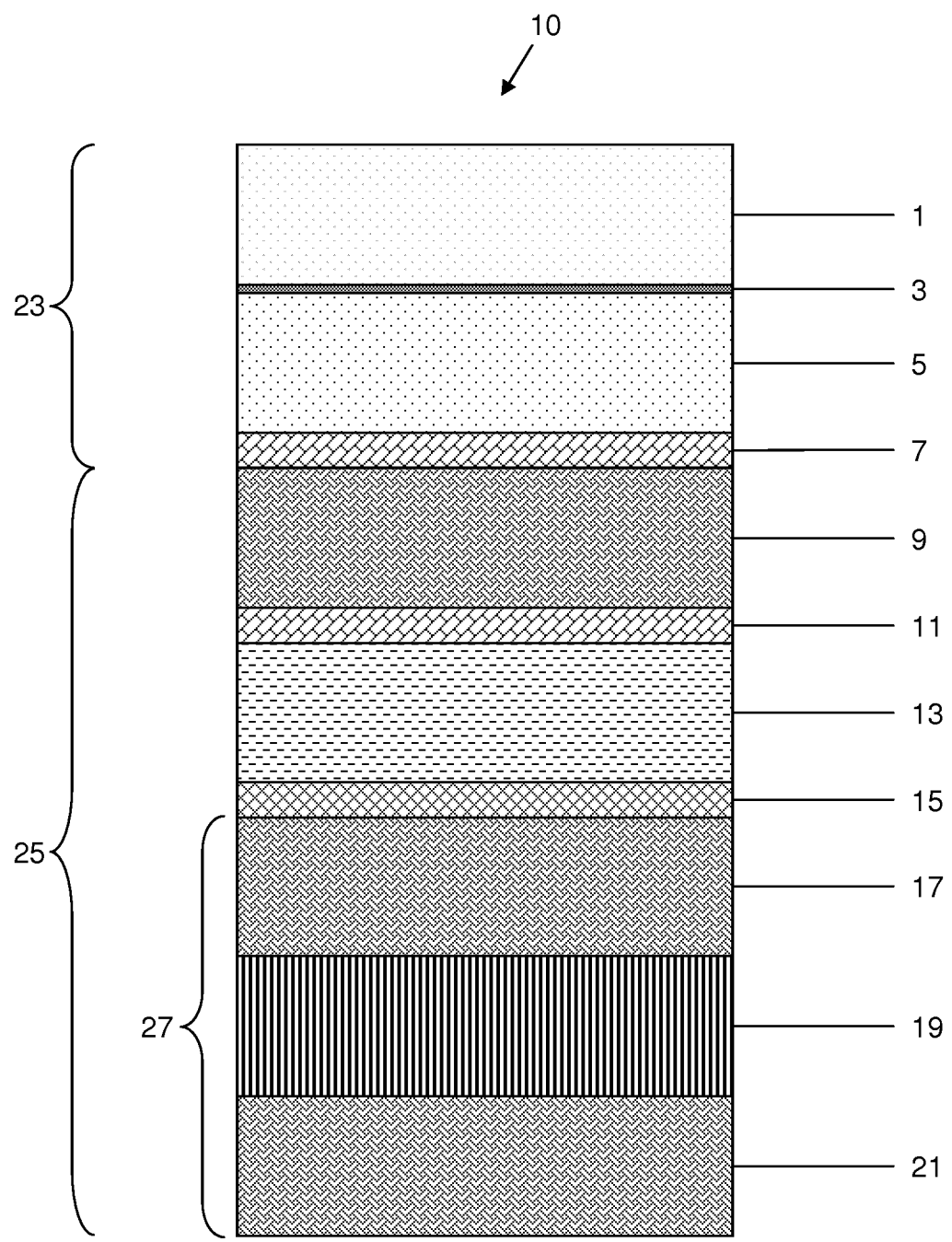
FIG. 3 shows a cross-sectional view of a third embodiment of the lid film.

FIG. 3 shows a cross-sectional view of a third embodiment of the lid film 10. In this embodiment, an alternative outer multi-layer film 23 is shown. The outer multi-layer film comprises a PET layer 1 and an $SiO_x$ coated PET 5 layer whereby the $SiO_x$ coating serves as a barrier layer 3.

Figure 4:
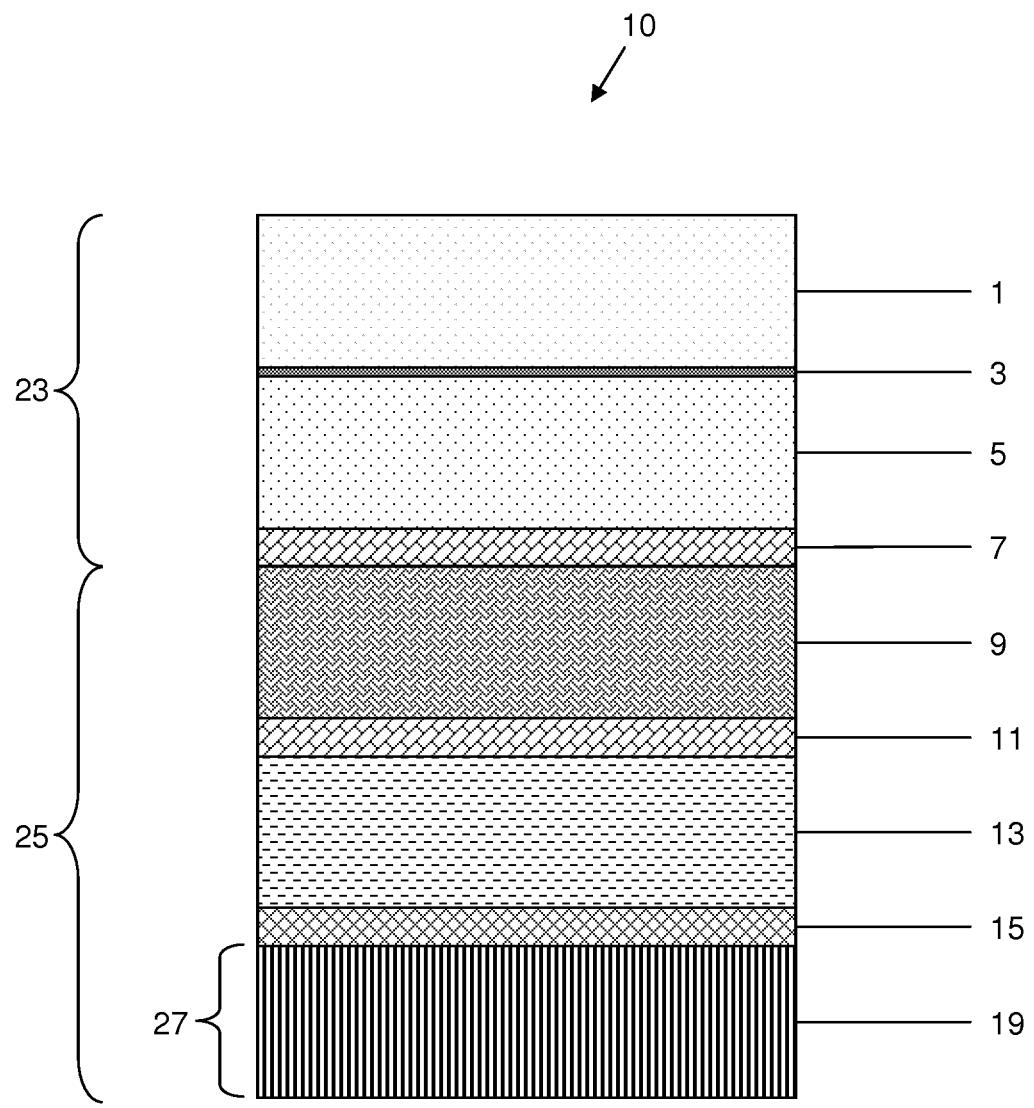
FIG. 4 shows a cross-sectional view of a fourth embodiment of the lid film.

FIG. 4 shows a cross-sectional view of a fourth embodiment of the lid film 10. The alternative outer multi-layer 23 comprising a $SiO_x$ coating as a barrier layer 3 interposed between the outer PET layer 1 and the inner PET layer 5 is bonded by means of an adhesive layer 7 to a coextruded inner multi-layer film 25 which comprises a single layered permeable layer 27. Said permeable layer 27 consisting of the single core layer 19 is sealed to the container (not shown) and thus faces a product space (not shown).

In the tables 1 and 2 below the results of evaporation experiments with two different volatile substances compositions Fragrance A and Fragrance B are shown. The values illustrate the weight loss over time in weight-%. Fragrance A is "Herbal Lavender" and fragrance B "Fruity Floral". Both fragrances are artificial mixtures of different aromatic volatile substances. The main components of Fragrance A are Ethyl Linalool (also 3,7-dimethyl-6-nonadien-3-ol) CAS N. 10339-55-6, Lanvandin Grosso France Oil (also Lavandula Hybrida Oil) CAS N. 8022-15-9, Isocyclocitral (also 3-Cyclohexene-1-carboxaldehyde), CAS #1335-66-6, and Dimyrcetol (also 2,6-Dimethyloct-7-en-2-yl formate+2,6-dimethyloct-7-en-2-ol) CAS N. 18479-58-8/25279-09-8. The main components of Fragrance B are Agrumex HC [also 2-(1,1-dimethyl ethyl) cyclohexanol acetate] CAS N. 88-41-5, Frutonil (also 2-Methyldecanonitrile) CAS N. 69300-15-8, Benzyl Acetate CAS N. 140-11-4, Allyl Caproate (also Allyl Hexanoate) CAS N. 123-68-2

The composition of the permeable layers A, B and C are as follows:

| Permeable Layer | outer layer EL % mVLDLLDPE | EL % LLDPE | EL % LDPE | EL Thickness (microns) |
| --- | --- | --- | --- | --- |
| A | 30 | 60 | 10 | 15 |
| B | 10 | 80 | 10 | 15 |
| C | 30 | 60 | 10 | 10 |

-continued

| Permeable Layer | core layer Core % mVLDLLDPE | Core %LLDPE | Core Thickness (microns) |
|---|---|---|---|
| A | 65 | 35 | 70 |
| B | 65 | 35 | 55 |
| C | 65 | 35 | 50 |

| Permeable Layer | sealing layer SL % mVLDLLDPE | SL % LLDPE | SL % LDPE | SL Thickness (microns) |
|---|---|---|---|---|
| A | 30 | 60 | 10 | 15 |
| B | 30 | 60 | 10 | 30 |
| C | 30 | 60 | 10 | 10 |

| Permeable Layer | total Caliper [microns] | mVLDLLDPE content [%] |
|---|---|---|
| A | 100 | 54.5 |
| B | 100 | 46.3 |
| C | 70 | 55.0 |

TABLE 1

Weight Loss in % (Fragrance A)

| Time | 0 days | 3 days | 7 days | 14 days |
|---|---|---|---|---|
| reference membrane | 0 | 3.4 | 6.8 | 11.8 |
| permeable layer A | 0 | 6.6 | 18.6 | 32.0 |
| permeable layer B | 0 | 2.8 | 14.0 | 23.8 |
| permeable layer C | 0 | 10.4 | 22.4 | 39.2 |
| No layer | 0 | 21.2 | 46.2 | 68.6 |

TABLE 2

Weight Loss in % (Fragrance B)

| Time | 0 days | 3 days | 7 days | 14 days |
|---|---|---|---|---|
| reference membrane | 0 | 7.2 | 16.6 | 28.6 |
| permeable layer A | 0 | 18.0 | 42.2 | 65.6 |
| permeable layer B | 0 | 15.6 | 35.2 | 57.4 |
| permeable layer C | 0 | 22.0 | 46.4 | 71.2 |
| No layer | 0 | 23.4 | 51.8 | 74.2 |

The reference membranes are membranes that have been obtained from commercially available air freshener cartridges and these reference membranes have a thickness of approximately 100 microns.

The invention claimed is:

1. Container for emanating volatile substances, comprising a container body having at least one opening closed by a lid film, said lid film comprising an outer multi-layer film having at least one barrier layer impermeable to the volatile substances, a coextruded inner multi-layer film having at least one permeable layer that is permeable to the volatile substances, the coextruded inner multi-layer film being bonded on one side to the outer multi-layer film and on another side to the container, the coextruded inner multi-layer film consisting of at least a polyethylene layer, a release layer comprising a polymer selected from the group consisting of EVOH and PETg, a peelable interface interposed between the release layer and said permeable layer, whereby said permeable layer comprises a polymer selected from the group consisting of mVLDLLDPE, ethylene vinyl acetate copolymer, and ethylene n-butyl acrylate copolymer, said permeable layer being sealed to the container and providing an evaporation rate of the volatile substances of at least 30% of a maximal evaporation rate of said at least one opening of said container body not covered by said permeable layer.

2. Container according to claim 1, characterized in that the evaporation rate of the volatile substances is at least 40% of a maximal evaporation rate of said at least one opening of said container body not covered by said permeable layer.

3. Container according to claim 1, characterized in that the permeable layer comprises an outer layer made of a polymer blend of mVLDLLDPE, LDPE, and LLDPE, a core layer made of a polymer blend of mVLDLLDPE, and LDPE or LLDPE, and a sealing layer made of a polymer blend of mVLDLLDPE, LDPE, and LLDPE.

4. Container according to claim 3, characterized in that the polymer blend of the outer layer comprises 10-30 weight-% mVLDLLDPE, 60-80 weight-% LLDPE, and 10 weight-% LDPE, the polymer blend of the core layer comprises 30-65 weight-% mVLDLLDPE, and 35-70 weight-% LLDPE, and the polymer blend of the sealing layer comprises 10-30 weight-% mVLDLLDPE, 60-80 weight-% LLDPE, and 10 weight-% LDPE, whereby the total content of mVLDLLDPE in the permeable layer is in the range of 10-90 weight percent.

5. Container according to claim 1, characterized in that the permeable layer comprises an optional outer layer made of LDPE or LLDPE, a core layer made of a polymer blend of EVA, PE, and an optional sealing layer made of LDPE or LLDPE.

6. Container according to claim 5, characterized in that the core layer consists of a blend of EVA in the range of 10-90 weight-%, and the remainder PE.

7. Container according to claim 1, characterized in that the permeable layer comprises an optional outer layer made of LDPE or LLDPE, a core layer made of a polymer blend of EBA, PE, and an optional sealing layer made of LDPE or LLDPE.

8. Container according to claim 7, characterized in that the core layer consists of a blend of EBA in range of 10-90 weight-%, and the remainder PE.

9. Container according to claim 1, characterized in that the outer multi-layer film comprises a first PET layer, an aluminum layer as barrier layer to the volatile substances, and a second PET layer.

10. Container according to claim 1, characterized in that the outer multi-layer film comprises a PET layer and a transparent barrier layer to the volatile substances.

11. Container according to claim 10, characterized in that the outer multi-layer film comprises a PET layer and PET-SiO$_x$ layer as barrier layer to the volatile substances.

12. Container according to claim 10, characterized in that the outer multi-layer film comprises a PET layer and PET-AlO$_x$ layer as barrier layer to the volatile substances.

13. Container according to claim 1, characterized in that the outer multi-layer film comprises a metalized PET layer, as barrier layer to the volatile substances.

14. Container according to claim 1, characterized in that there is a small non-bonded region between the release layer and the permeable layer providing a grip tab for separating the lid film between these two layers.

\* \* \* \* \*